US011504412B2

(12) United States Patent
Clarke et al.

(10) Patent No.: US 11,504,412 B2
(45) Date of Patent: Nov. 22, 2022

(54) BETA-CASEINS AND COGNITIVE FUNCTION

(71) Applicant: THE A2 MILK COMPANY LIMITED, Auckland (NZ)

(72) Inventors: Andrew John Clarke, Auckland (NZ); Gregory Wayne Yelland, Waveley (AU)

(73) Assignee: THE A2 MILK COMPANY LIMITED, Auckland (NZ)

( * ) Notice: Subject to any disclaimer, the term of this patent is extended or adjusted under 35 U.S.C. 154(b) by 0 days.

(21) Appl. No.: 16/084,853

(22) PCT Filed: Mar. 29, 2017

(86) PCT No.: PCT/NZ2017/050035
§ 371 (c)(1),
(2) Date: Sep. 13, 2018

(87) PCT Pub. No.: WO2017/171563
PCT Pub. Date: Oct. 5, 2017

(65) Prior Publication Data
US 2019/0083567 A1 Mar. 21, 2019

Related U.S. Application Data

(60) Provisional application No. 62/315,441, filed on Mar. 30, 2016.

(51) Int. Cl.
| | |
|---|---|
| A61K 38/01 | (2006.01) |
| A61K 35/20 | (2006.01) |
| A61P 25/28 | (2006.01) |
| A23L 33/19 | (2016.01) |
| A23C 9/152 | (2006.01) |
| A23K 20/147 | (2016.01) |
| A23C 9/20 | (2006.01) |

(52) U.S. Cl.
CPC .......... A61K 38/018 (2013.01); A23C 9/1526 (2013.01); A23C 9/20 (2013.01); A23K 20/147 (2016.05); A23L 33/19 (2016.08); A61K 35/20 (2013.01); A61P 25/28 (2018.01); A23V 2002/00 (2013.01); A23V 2200/322 (2013.01); A23V 2250/54246 (2013.01)

(58) Field of Classification Search
CPC ...... A61K 38/018; A61K 38/01; A61K 35/20; A23L 33/19; A61P 25/28
USPC ......................................... 514/5.7; 530/360
See application file for complete search history.

(56) References Cited

U.S. PATENT DOCUMENTS

| | | | | |
|---|---|---|---|---|
| 6,451,368 | B1 * | 9/2002 | Elliott | A23C 9/20 426/580 |
| 7,157,616 | B2 * | 1/2007 | Elliott | A23C 9/20 800/15 |
| 2010/0166859 | A1 * | 7/2010 | Edens | A61K 38/06 424/474 |

FOREIGN PATENT DOCUMENTS

| | | |
|---|---|---|
| RU | 2161500 C1 | 1/2001 |
| WO | WO-1996/014577 A1 | 5/1996 |
| WO | WO-1996/036239 A1 | 11/1996 |
| WO | WO-2002/019832 A1 | 3/2002 |
| WO | WO-2014/193248 A1 | 12/2014 |
| WO | WO-2015/005804 A1 | 1/2015 |
| WO | WO-2015/026245 A1 | 2/2015 |
| WO | WO-2015/187795 A1 | 12/2015 |
| WO | WO-2016/190750 A1 | 12/2016 |

OTHER PUBLICATIONS

Pasin, Gonca, "A2 Milk Facts" from cdrf.org, cdrf.org/2017/02/09/a2-milk-facts/, pp. 1-3. (Year: 2017).*
Satyanarayana KV, "The hype over branded A2 milk," The Hindu Business Line, pp. 1-6. Published Apr. 19, 2018. (Year: 2018).*
Hirst K. Kris, "History of the Domestication of Cows and Yaks," https://www.thoughtco.com/history-of-the-domestication-of-cows-170652?print, pp. 1-8. (Year: 2019).*
Bruce et al, "Validity of a screeing tool for detecting subtle cognitive impairment in the middle-aged and elderly," Clinical Interventions in Aging, 9: 2165-6276. (Year: 2014).*
Jianqin et al., :Effects of milk containing only A2 beta casein versus milk containing both A1 and A2 beta casein proteins on gastrointestinal physiology, symptoms of discomfort, and cognitive behavior with self-reported . . . , Nutrition Journal 15, Article No. 35 (2015), pp. 1-32 as enclosed (Year: 2015).*
Yogurt from https://www.pccmarkets.com/sound-consumer/2011-07/yogurt, pp. 1-4. Publication date Jul. 2011. (Year: 2011).*
"Effects Comparison of A1 and A2 Milk on Gastrointestinal Physiology, Symptoms and Cognitive Behavior," from clinicaltrials.gov, NCT02406469, pp. 1-8. study completion date: Feb. 2015. (Year: 2015).*
Bruce et al., Validity of a screening tool for detecting subtle cognitive impairment in the middle-aged and elderly, *Clin. Interv. Aging.* 9:2165-76 (2014).
Cade et al., Autism and Schizophrenia: Intestinal Disorders, *Nutr. Neurosci.* 3:57-72 (2000).
Dohan, Genetic hypothesis of idiopathic schizophrenia: its exorphin connection, *Schizophr Bull.* 14:489-94(1988).
Dubynin et al., Delayed effect of exorphins on learning of albino rat pups, *Biology Bulletin.* 35:43-49 (2008).
International Preliminary Report on Patentability, PCT/NZ2017/050035 (dated Oct. 2, 2018).

(Continued)

*Primary Examiner* — Julie Ha
(74) *Attorney, Agent, or Firm* — Marshall, Gerstein & Borun LLP

(57) ABSTRACT

The disclosure provides a method of improving the cognitive function of an animal by providing a composition containing beta-casein, wherein at least 75% by weight of the beta-casein is a beta-casein variant that does not produce BCM-7 on digestion in the gut of the animal.

10 Claims, 5 Drawing Sheets

(56) References Cited

OTHER PUBLICATIONS

International Search Report and Written Opinion, PCT/NZ2017/050035 (dated Jul. 5, 2017).
Kawashti et al., Possible immunological disorders in autism: concomitant autoimmunity and immune tolerance, *Egypt J. Immunol.* 13:99-104 (2006).
Kost et al., Beta-casomorphins-7 in infants on different type of feeding and different levels of psychomotor development, *Peptides.* 30:1854-60 (2009).
Maklakova et al., [The effect of beta-casomorphin-7 on the level of food and defense motivations in different types of learning], *Zh Vyssh Nerv Deiat Im I P Pavlova.* 45:1143-50 (1995).
Niebuhr et al., Association between bovine casein antibody and new onset schizophrenia among US military personnel, *Schizophr Res.* 128:51-5 (2011).
Reichelt et al., Can the pathophysiology of autism be explained by the nature of the discovered urine peptides? *Nutr. Neurosci.* 6:19-28 (2003).
Reichelt et al., Gluten, milk proteins and autism:dietary intervention effects on behavior and peptide secretion, *J. Appr. Nutr.* 42:1-11 (1990).
Reichelt et al., Specific IgA antibody increases in schizophrenia, *Biol. Psychiatry.* 37:410-3 (1995).
Severance et al., Dietary antigens, epitope recognition, and immune complex formation in recent onset psychosis and long-term schizophrenia, *Schizophr. Res.* 126:43-50 (2011).
Severance et al., Subunit and whole molecule specificity of the anti-bovine casein immune response in recent onset psychosis and schizophrenia, *Schizophr Res.* 118:240-7 (2010).
Sokolov et al., Autistic children display elevated urine levels of bovine casomorphin-7 immunoreactivity, *Peptides.* 56:68-71 (2014).
Sun et al., A Peptide found in schizophrenia and autism causes behavioral changes in rats, *Autism.* 3:85-95 (1999).
Sun et al., b-casomorphin induces induces Fos-like immunoreactivity in discrete brain regions relevant to schizophrenia and autism, *Autism.* 3:67-83 (1999).
Tveiten et al., Peptides and exorphins in the autism spectrum, *Open J. Psychiatry.* 3:275-87 (2014).

* cited by examiner

BETA-CASEINS AND COGNITIVE FUNCTION

TECHNICAL FIELD

The invention relates to the milk protein beta-casein and improving cognitive function in animals. In particular, the invention relates to milk and milk derived food products having a beta-casein composition that is predominantly A2 beta-casein or related beta-casein variants. The applicant has found that the consumption of milk containing the A1 variant of beta-casein is associated with decreased cognitive processing speed and accuracy whereas the consumption of milk containing only the A2 variant of beta-casein is associated with increased processing speed and accuracy.

BACKGROUND OF THE INVENTION

Milk, mainly bovine milk, consumed in populations throughout the world, is a major source of protein in human diets. Bovine milk typically comprises around 30 grams per litre of protein. Caseins make up the largest component (80%) of that protein, and beta-caseins make up about 37% of the caseins. In the past two decades the body of evidence implicating casein proteins, especially beta-caseins, in a number of adverse physiological or biological actions and health disorders has been growing.

The beta-caseins can be categorised as A1 beta-casein and A2 beta-casein. These two proteins are the predominant beta-caseins in the bovine milk consumed in most human populations. A1 beta-casein differs from A2 beta-casein by a single amino acid. A histidine amino acid is located at position 67 of the 209 amino acid sequence of A1 beta-casein, whereas a proline is located at the same position of A2 beta-casein. This single amino acid difference is, however, critically important to the enzymatic digestion of beta-caseins in the gut. The presence of histidine at position 67 allows a protein fragment comprising seven amino acids, known as beta-casomorphin-7 (BCM-7), to be produced on enzymatic digestion. Thus, BCM-7 is a digestion product of A1 beta-casein. In the case of A2 beta-casein, position 67 is occupied by a proline which hinders cleavage of the amino acid bond at that location. Thus, BCM-7 is not a digestion product of A2 beta-casein.

Other beta-casein variants, such as the B, C, F, G and H1 variants, also have histidine at position 67, whereas variants in addition to the A2 variant, such as the A3, D, E, H2 and I variants, have proline at position 67. But these variants are found only in very low levels, or not found at all, in milk from cows of European origin. Thus, in the context of this invention, the term A1 beta-casein may refer to any beta-casein having histidine at position 67, and the term A2 beta-casein may refer to any beta-casein having proline at position 67.

BCM-7 is an opioid peptide and can bind to and activate opioid receptors throughout the body. BCM-7 has the ability to cross the gastrointestinal wall and enter circulation enabling it to influence systemic and cellular activities via opioid receptors. The applicant and others have previously determined an adverse association between the consumption of A1 beta-casein found in milk or milk products and type I diabetes,[1] coronary heart disease,[2] neurological disorders,[3] inflammation of the bowel,[4] the symptoms of lactose intolerance[5] and the regulation of blood glucose levels.[6] The growing body of scientific evidence linking beta-casein variants to these diseases and disorders has led the applicant to investigate a range of physiological and behavioural effects of beta-casein consumption.

The consumption of milk containing a beta-casein variant having histidine, rather than proline, at position 67 has been reported to cause the release of an opioid peptide, or exorphin, which may induce or aggravate neurological disorders such as autism or Asperger's syndrome.[7] This opioid has been identified as BCM-7. Several studies have reported a link between casein and autism spectrum disorders, including elevated urinary peptide and exorphin secretion, and the presence of antibodies to casein and BCM-7 in individuals with autism.[8-13] Associations between casein, particularly antibodies to casein, and schizophrenia have also been reported.[14-18] Because BCM-7 interacts with opioid and serotonin receptors, which are involved in synaptogenesis and central signalling processes, prolonged exposure to BCM-7 may have adverse effects on brain development and function leading to the manifestation of neurological diseases or conditions.[12]

It has been reported that BCM-7 significantly reduces normal behaviours in rats, such as rearing, walking and grooming, and enhanced abnormal activities, such as explosive motor behaviour, circling and decreased social interaction.[19] It has been determined that these behavioural effects of BCM-7 are caused by its interaction with opioid receptors because the effects were abolished by the specific opiate receptor antagonist naloxone. BCM-7 also induced fos-like immunoreactivity in brain regions relevant to schizophrenia, particularly the prefrontal cortex, the nucleus accumbens, the bed nucleus of the stria terminalis, and the caudate-putamen.[20]

BCM-7 may also affect other neurological activities, including psychomotor development.[21] Immunoreactivity of human and bovine BCM-7 has been detected in breast-fed and formula-fed infants, respectively, within the first three months of life.[22] Notably, elevated bovine BCM-7 immunoreactivity was associated with delayed psychomotor development and abnormally high muscle tone.

These reported findings all relate to the influence of BCM-7, or the beta-casein variants that produce BCM-7 upon digestion, on behavioural characteristics of individuals suffering from clinically diagnosed diseases or conditions. The findings do not relate to healthy individuals. Further, it is well-known that the outcome of studies based on cell culture experiments cannot reliably be extrapolated to in vivo or clinical effects since there are many variables relating to BCM-7 production, transport and metabolism that affect tissue exposure and therefore biological response. For example, it is known that the concentrations of opioids and their affinity to opioid receptors are important for cell response.

In its ongoing investigations into links between beta-casein variants and biological response in humans, the applicant has now found an adverse association between A1 beta-casein (and other beta-casein variants that produce BCM-7) on two specific aspects or measures of cognitive function of healthy people. It is well-known to those skilled in the field of psychology and related disciplines that behaviour is distinct from cognition. Behaviour is regarded as a consequence of environmental stimuli, whereas cognition relates to information processing affecting how humans perceive, remember and understand the world around them. Factors that influence behaviour do not ordinarily affect cognitive function, nor would they be expected to affect cognitive function. The applicant's research represents the first conclusive scientific evidence of a direct link between the consumption of beta-casein variants and cognitive function.

It is therefore an object of the invention to provide a method for improving cognitive function in humans and other animals, or to at least provide a useful alternative to existing methods.

SUMMARY OF THE INVENTION

In a first aspect of the invention there is provided a method of improving the cognitive function of an animal by ingesting a composition containing beta-casein or by providing to an animal a composition containing beta-casein, wherein at least 75% by weight of the beta-casein is a beta-casein variant that does not produce BCM-7 on digestion in the gut of the animal.

In certain embodiments of the invention the beta-casein variant is A2 beta-casein, A3 beta-casein, D beta-casein, E beta-casein, H2 beta-casein or I beta-casein. In preferred embodiments the beta-casein variant is A2 beta-casein. The amount of A2 beta-casein may be any amount in the range of 75% to 100% by weight of the beta-casein, for example at least 90% or even 100%.

In certain embodiments of the invention improved cognitive function is assessed using any one or more of Subtle Cognitive Impairment Test (SCIT), Automated Cognitive Test (ACT), Automated Neuropsychological Assessment Metrics (ANAM), Cognitive Drug Research Computerised Assessment System for Dementia (COGDRAS-D), Community Screening Instrument for Dementia (CSI-D), Computer-Administered Neuropsychological Screen for Mild Cognitive Impairment (CANS-MCI), Computer Assessment of Mild Cognitive Impairment (CAMCI), Computerised Self-Test (CST), Florida Brief Memory Scale (FBMS), Mild Cognitive Impairment (MCI), Neuropsychological Test Battery (NTB), Brief Assessment of Cognition in Schizophrenia (BACS), Cambridge Mental Disorders of the Elderly Examination-Revised (CAMDEX-R), Cambridge Neuropsychological Test Automated Battery (CANTAB), Computerised Multiphasic Interactive Neurocognitive Dual Display System (CMINDS), Computerised Neuropsychological Test Battery (CNTB), Memory Capacity Test (MCT), Neuropsychological Assessment Battery (NAB), Alzheimer's Disease Cooperative Study (ADCS), Executive, Linguistic, Spatial and Memory Abilities Battery (ELSMEM), Mini Mental State Examination (MMSE), and Hamilton D cognitive test (HAM-D).

In certain embodiments of the invention the composition is milk or a milk product. The milk may be fresh milk, milk powder, liquid milk reconstituted from powder, skim milk, homogenised milk, condensed milk, evaporated milk, pasteurised milk, or non-pasteurised milk. The milk product may be infant formula, cream, yoghurt, quark, cheese, butter, ice cream, or any other milk product.

In a second aspect of the invention there is provided a composition for improving cognitive function in an animal which composition contains beta-casein, wherein at least 75% by weight of the beta-casein is a beta-casein variant that does not produce BCM-7 on digestion in the gut of the animal.

In another aspect of the invention there is provided the use of milk in the manufacture of a composition for improving cognitive function in an animal where the milk contains beta-casein and where at least 75% by weight of the beta-casein is a beta-casein variant that does not produce BCM-7 on digestion in the gut of the animal.

In a further aspect of the invention there is provided a method of preventing or treating cognitive impairment in an animal comprising the ingestion by the animal of a composition containing beta-casein or by providing to the animal a composition containing beta-casein, wherein at least 75% by weight of the beta-casein is a beta-casein variant that does not produce BCM-7 on digestion in the gut of the animal.

DETAILED DESCRIPTION

Figure 1:
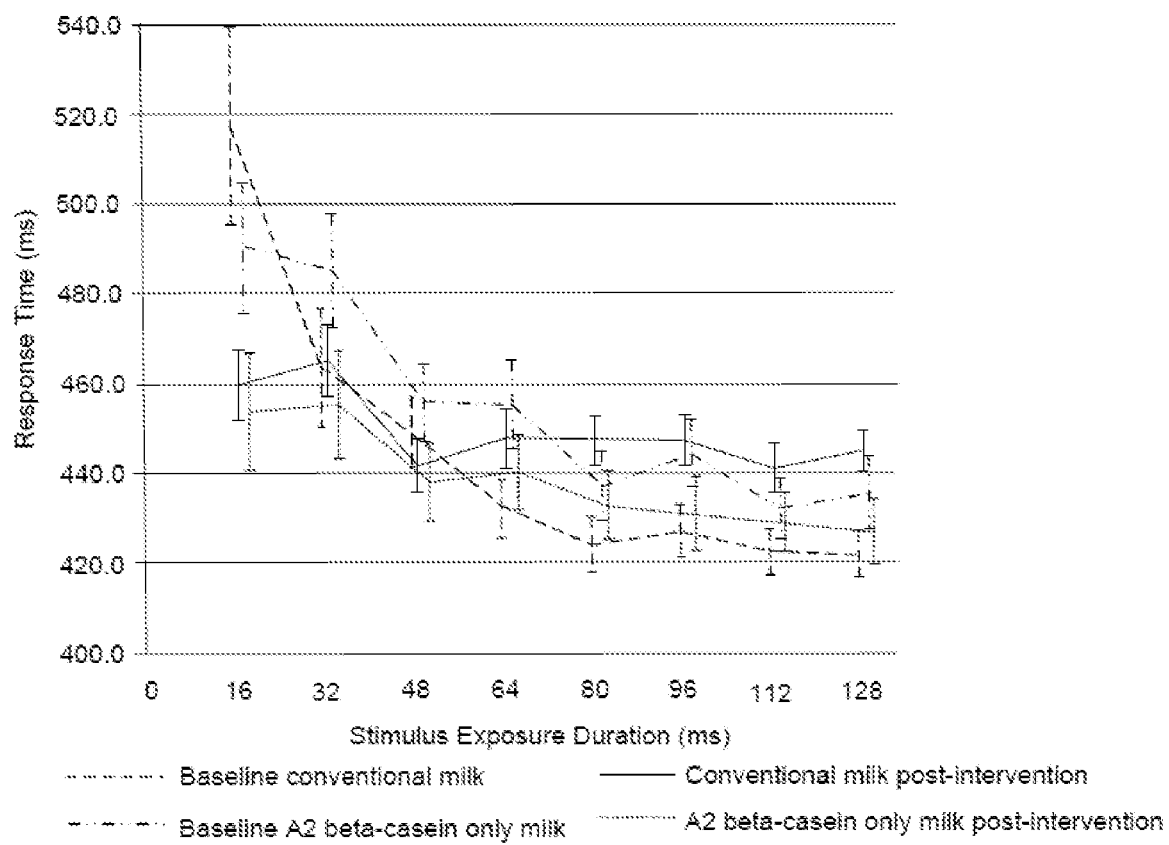
FIG. 1 shows SCIT response time for Phase 1 feeding intervention of the adult trial.

The invention relates to a composition containing the protein beta-casein and its use for improving cognitive function in animals, especially humans. Importantly, the beta-casein is the A2 variant of beta-casein, or makes up at least 75% by weight of the total beta-casein variants present in the composition. The importance of the predominance of the A2 variant in the composition is due to the fact that the applicant has shown that there is a direct link between consumption of the A1 variant and reduced cognitive function in humans, specifically response time and error rate in the Subtle Cognitive Impairment Test. Additionally the applicant has shown that there is a direct link between consumption of the A2 variant and improved cognitive function independent of the effect of avoidance of consumption of the A1 variant.

The term "cognitive function" or "cognition" is intended to mean a group of mental processes that includes attention, memory, production and understanding of language, learning, reasoning, problem solving, and decision making.

The term "beta-casomorphin-7" or "BCM-7" refers to the protein fragment Tyr-Pro-Phe-Pro-Gly-Pro-Ile, a heptapeptide produced on enzymatic digestion of bovine beta-casein variants that have a histidine, rather than a proline, at position 67 of the amino add sequence.

Since the primary, if not only, source of beta-caseins in the diet of most human populations is milk or products derived from milk, and since most milk consumed contains a mixture of the A1 and A2 variants of beta-casein only, the consumption of milk (or products made from such milk) having a high content of the A2 variant will necessarily mean that the consumption of the A1 variant is low. Thus, if the only dietary source of beta-casein contains the A2 variant and no other variant, the dietary intake of the A1 variant is eliminated and the adverse effect of BCM-7 on cognitive function can therefore also be expected to be eliminated.

Accordingly, the invention of this application is based on the reduction or elimination of A1 beta-casein in the diet, and the promotion of A2 beta-casein. This is achieved by ensuring that the beta-casein in beta-casein containing food compositions, especially milk and milk products, is predominantly or even exclusively A2 beta-casein.

Ideally, the beta-casein in the composition is 100% A2 beta-casein. The complete elimination of A1 beta-casein therefore reduces the potential for cognitive impairment. However, cognitive impairment may be enhanced by any composition where the beta-casein is predominantly A2 beta-casein, for example, any amount between 75% by weight and 100%, including but not limited to 80%, 90%, 95%, 98% and 99% by weight.

The composition of the invention is typically milk, but may also be any milk-derived product such as cream, yoghurt, quark, cheese, butter, or ice cream. The composition may also be a non-milk product containing beta-casein that has been obtained from milk. The composition may be beta-casein itself, or may be prepared from beta-casein, which beta-casein may be in solid form such as powder or granules or in the form of a solid cake.

While the milk may be obtained from any mammal, including humans, goats, pigs and buffalo, in preferred embodiments of the invention the milk is bovine milk.

The milk may be in the form of fresh milk, milk powder, liquid milk reconstituted from a powder, skim milk, homogenised milk, condensed milk, evaporated milk, pasteurised milk or non-pasteurised milk, or any other form of milk.

The composition of the invention is applicable for consumption by humans primarily, but it should be appreciated that the health benefit is also relevant for some other animals such as cats, dogs and other domestic animals.

Support for the invention is found in Example 1 which describes a trial where adult subjects were assigned to take milk containing both A1 and A2 beta-caseins (referred to as conventional milk) and milk containing A2 beta-casein but no other beta-casein variant (referred to as A2 beta-casein only milk). Cognitive function was assessed using the Subtle Cognitive Impairment Test (SCIT), which is a computer-based test that measures the speed and effectiveness of information processing. SCIT analysis showed that consumption of conventional milk was associated with highly significant increases in response time and error. The increases in response time were primarily found for the longer stimulus durations (the tail) while increases in error rate were largely restricted to the shorter stimulus durations (the head). This suggests that the consumption of conventional milk is associated with reduced efficiency of preconscious automatic processing, but the longer stimulus duration-controlled processes help to reduce the deficit in processing efficiency at the cost of processing speed. This minor impairment of cognitive function can have a considerable impact in situations where rapid stimulus detection and/or rapid decision making are required. This finding demonstrates that the consumption of milk containing A1 beta-casein impacts on cognitive function.

While experiments were conducted using the SCIT, it will be understood by those skilled in the art that any other suitable test for cognitive function may be used. Examples include Automated Cognitive Test (ACT), Automated Neuropsychological Assessment Metrics (ANAM), Cognitive Drug Research Computerised Assessment System for Dementia (COGDRAS-D), Community Screening Instrument for Dementia (CSI-D), Computer-Administered Neuropsychological Screen for Mild Cognitive Impairment (CANS-MCI), Computer Assessment of Mild Cognitive Impairment (CAMCI), Computerised Self-Test (CST), Florida Brief Memory Scale (FBMS), Mild Cognitive Impairment (MCI), Neuropsychological Test Battery (NTB), Brief Assessment of Cognition in Schizophrenia (BACS), Cambridge Mental Disorders of the Elderly Examination-Revised (CAMDEX-R), Cambridge Neuropsychological Test Automated Battery (CANTAB), Computerised Multiphasic Interactive Neurocognitive Dual Display System (CMINDS), Computerised Neuropsychological Test Battery (CNTB), Memory Capacity Test (MCT), Neuropsychological Assessment Battery (NAB), Alzheimer's Disease Cooperative Study (ADCS), Executive, Linguistic, Spatial and Memory Abilities Battery (ELSMEM), Mini Mental State Examination (MMSE), and the Hamilton D cognitive test (HAM-D).

As noted above, several studies have revealed associations between A1 beta-casein/BCM-7 and clinically diagnosed neurological conditions, such as autism and schizophrenia. It has also been reported that elevated BCM-7 immunoreactivity is associated with delayed psychomotor development in infants. The data of Example 1 imply that A1 beta-casein and its peptide derivatives also affect information processing in the brain in healthy subjects. Information processing in the brain of healthy subjects is unrelated to the effects of diagnosed neurological conditions. Thus, an association between a protein (or any other substance) and information processing in the brain of healthy subjects is not considered to be predictable from an association between the same protein (or other substance) and a neurological condition.

Figure 2:
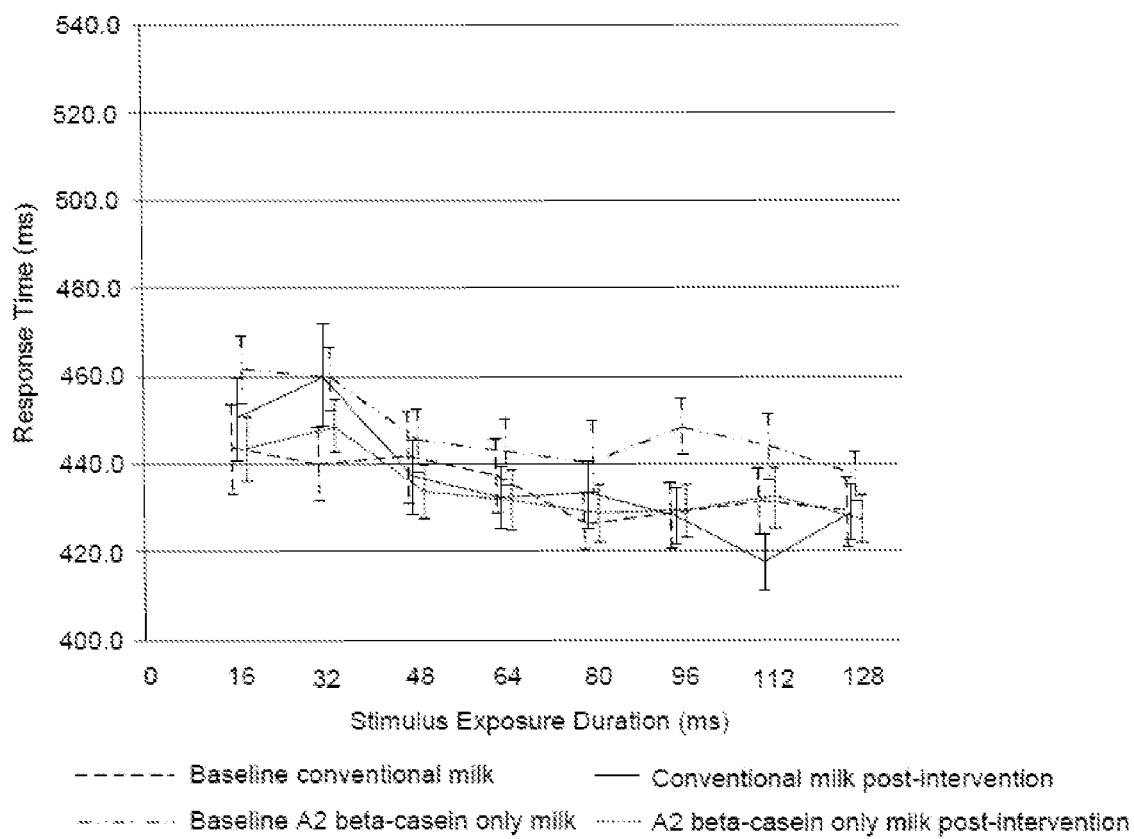
FIG. 2 shows SCIT response time for Phase 2 feeding intervention of the adult trial.

Summary statistics for SCIT response time at each exposure duration are shown in Table 2 by study phase and product. FIGS. 1 and 2 show the response time at each exposure duration (16, 32, 48, 64, 80, 96, 112 and 128 ms) by product in intervention phase 1 and phase 2, respectively.

Results of mixed effect ANOVA (Table 3) show that product effect was significant on both the response time (p=0.0013) and the error rate (p=0.0004) at each exposure duration. Significant product effect was also found in the tail mean of response time (p=0.027) and in the head mean of error rate (p=0.020). Baseline levels of all SCIT variables were significant covariates for the levels after product intervention.

Table 4 shows the results of contrast testing between the two study products. Subjects under intervention of conventional milk had an average of 8.6 ms longer response time (p=0.0013) and 1.76% more error rate (p=0.0004) compared to those under intervention of A2 beta-casein only milk. The tail mean of response time (at exposure duration of 80-128 ms) was 14.7 ms longer (p=0.020) and the head mean of error rate (at exposure duration of 16-64 ms) was 2.76% higher (p=0.027) with consumption of conventional milk than A2 beta-casein only milk, while no significant difference was observed in the head mean of response time and in the tail mean of error rate comparing the two products.

Figure 3:
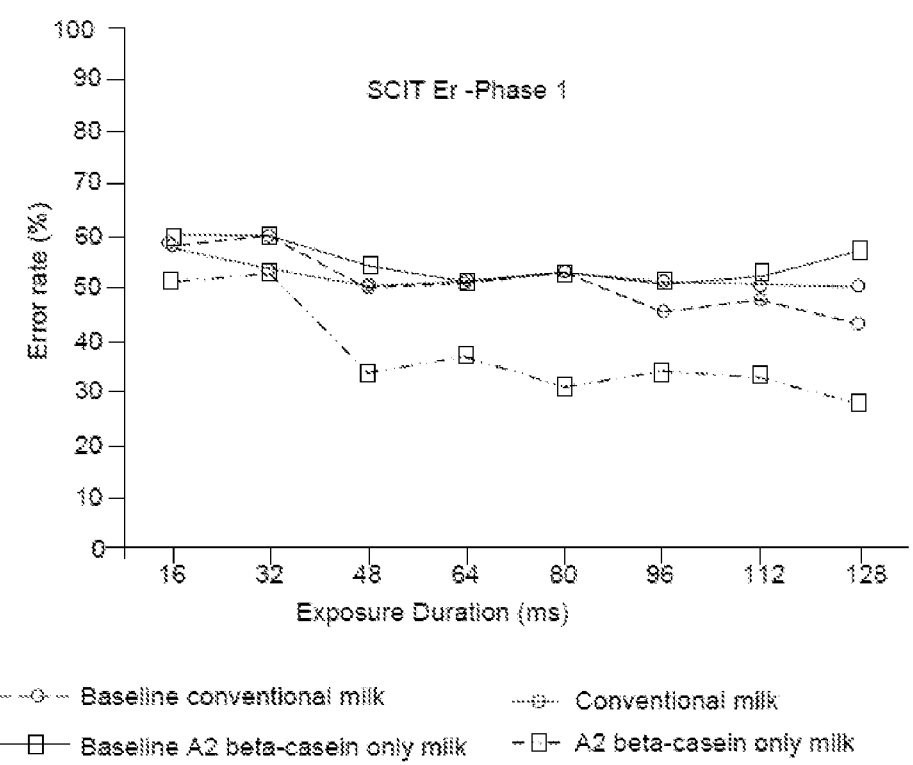
FIG. 3 shows the SCIT error rate for Phase 1 feeding intervention in the preschool trial.
Figure 4:
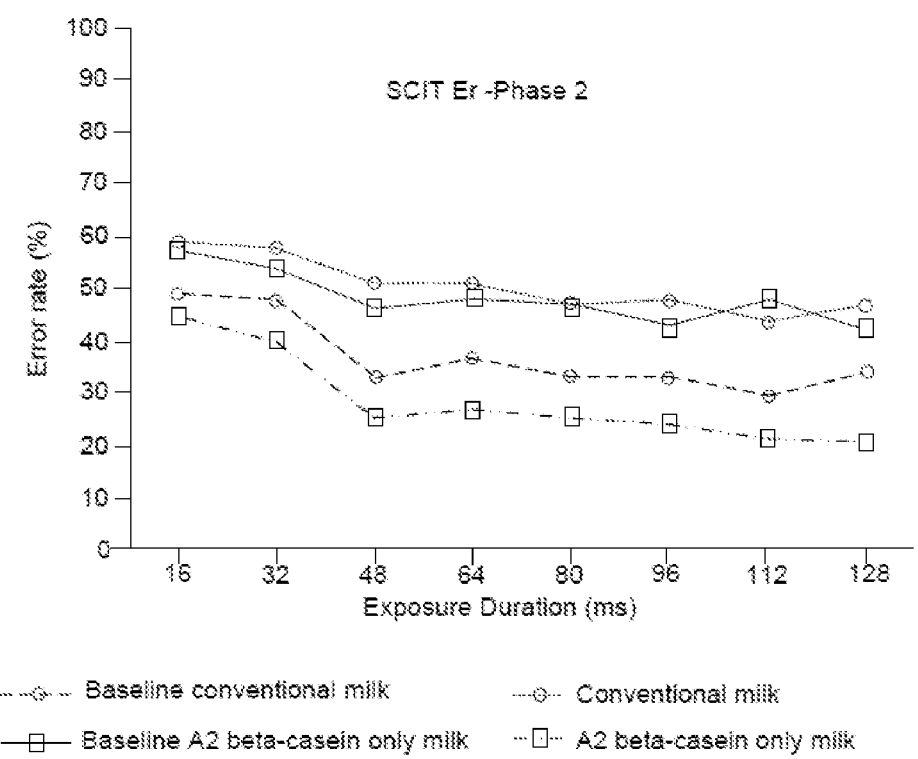
FIG. 4 shows the SCIT error rate for Phase 2 feeding interventions in the preschool trial.
Figure 5:
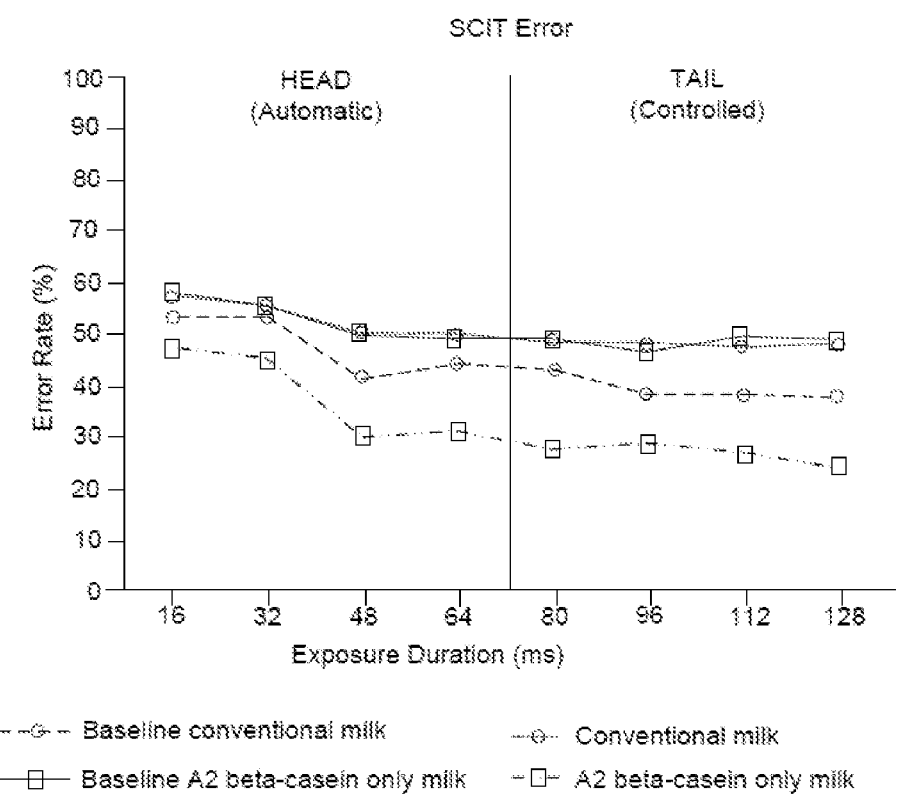
FIG. 5 shows the SCIT error rate of the Head and Tail exposure durations.

Example 2 is a study involving preschool-age children. The results are shown in FIGS. 3-5. For both head and tail error rates significant outcomes were observed for all three of the critical outcomes:

1. The Main Effect of Condition—indicates whether there is any effect of milk consumption on SCIT performance, but does not discriminate between milk types.
2. The interaction between Milk Type and Condition—indicates whether there is a difference between Milk Type in terms of SCIT performance pre- and post-milk consumption.
3. The interaction between Phase, Milk Type and Condition—indicates whether the order in which participants received Milk Types has any effect on SCIT performance pre- and post-milk consumption as a function of Milk Type.

There was a significant overall improvement in performance between baseline and post-milk consumption measures. However, this was primarily driven by a large improvement in error rates following consumption of A2 beta-casein only milk in the presence of an apparent increase in error rates following consumption of conventional milk. This observation is supported by a significant interaction between Milk Type and Condition. There is also a significant interaction between Phase, Milk Type and Condition. This is best illustrated in FIG. 3 for head and tail error rate data for the group of participants who consumed conventional milk in phase 1 and A2 beta-casein only milk in phase 2 (Group 1) relative to the group of participants who consumed A2 beta-casein only milk in phase 1 and conventional milk in phase 2 (Group 2). For Group 1, consuming conventional milk had no effect on error rates, but consuming A2 beta-casein only milk resulted in a large and significant decrease in error rates. For Group 2, consuming A2 beta-casein only milk in phase 1 resulted in a large and significant decrease in error rate following the consumption of A2 beta-casein only milk. However, for this group there was also a large and significant increase in errors following the subsequent consumption of conventional milk in phase 2. This is the outcome that gives rise to the phase×Milk Type×Condition interaction but does not represent the true effect of conventional milk. Rather, a carryover effect of having consumed A2 beta-casein only milk in the first phase was observed for the participants of Group 2. The improvement in error rates following the consumption of A2 beta-casein only milk continued over the washout period in the absence of A2 beta-casein only milk. When conventional milk was introduced, the performance of the participants returned to the equivalent of that for the no milk consumption baseline. Thus, the patterns of performance shown in the graphs for Group 1 for head and tail error rates is a better depiction of the effects of consuming conventional milk versus A2 beta-casein only milk, with the consumption of conventional milk having no effect on performance while the consumption of A2 beta-casein only milk improved the accuracy of performance on the SCIT relative to baseline performance. Further, improved accuracy of performance following the consumption of A2 beta-casein only milk continued in the absence of A2 beta-casein only milk for at least the 10 days of the washout period, and possibly longer.

These studies represent the first clear scientific evidence of a link between A1 beta-casein consumption and reduced cognitive function. Through the applicant's finding, it is clear that the consumption of beta-caseins that produce BCM-7 on digestion should be avoided. Additionally these studies represent the first clear scientific evidence of a link between A2 beta-casein consumption and improved cognitive function independent of the effects of the avoidance of A1 beta-casein consumption and subsequent BCM-7 production. Further, the continuation of improved performance accuracy after consuming the A2 beta-casein only milk is clear evidence of an ongoing beneficial effect of consuming A2 beta-casein for at least two weeks following consumption. Thus, the benefit of consuming beta-casein that does not produce BCM-7 on digestion extends well past the time taken for consumption and digestion.

In practical terms, the benefits of the invention can be achieved for large populations by sourcing milk having a beta-casein content that is predominantly A2 beta-casein and producing products derived from that milk, and making that milk and those products available for the purpose of improving, enhancing or maintaining cognitive function.

The milk of cows can be tested for the relative proportions of A1 beta-casein and A2 beta-casein. Alternatively, cows can be genetically tested for their ability to produce milk containing A1 beta-casein (or other variants capable of producing BCM-7) or tested for their ability to produce milk containing A2 beta-casein (or other variants incapable of producing BCM-7) or a combination of both. These techniques are well-known.

The present invention provides a solution that is comparatively easy to manage, i.e. avoidance of milk or milk products that contain A1 beta-casein and ensuring that milk and milk products in the diet contain beta-casein that is predominantly A2 beta-casein, preferably 100% A2 beta-casein.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following example. It will be appreciated that the invention as claimed is not intended to be limited in any way by this example.

EXAMPLES

Example 1: Milk Trial and SCIT Analysis in Adults

Study Design

The study was conducted in accordance with the Declaration of Helsinki as amended in Seoul 2008 and was approved by the ethics committee of the Shanghai Nutrition Society (approval number: SNSIRB #2014[002]). The study was registered with ClinicalTrials.gov (identifier: NCT02406469). All subjects provided written informed consent prior to inclusion in the study. This was a single-site, double-blind, randomised, controlled, 2×2 cross-over study designed to evaluate the effects of milk containing only the A2 beta-casein type versus milk containing the A1 and A2 beta-casein types on serum levels of immune response markers in correlation to symptoms of intolerance. After a screening visit at which the subjects underwent full clinical evaluations and qualitative tests for urinary galactose, eligible subjects entered a 2-week washout period. Then, subjects entered intervention period 1 in which they received milk containing only the A2 beta-casein variant (A2 beta-casein only milk) or milk containing both A1 and A2 beta-casein variants (conventional milk) according to the randomisation scheme for 2 weeks. After a second 2-week washout period, the subjects entered intervention period 2 in which they received the opposite milk product. Visits were scheduled at the start of each intervention period and at Days 7 and 14 in each intervention period. The subjects were contacted by telephone during each washout period. The study was conducted at the Department of Gastroenterology, Xin Hua Hospital Affiliated to Shanghai Jiao Tong University School of Medicine (Shanghai, China).

participate in another interventional clinical research study during the present study; did not meet any of the exclusion criteria; and fully understood the nature, objective, benefit, and the potential risks and side effects of the study. Subjects were recruited via advertisements placed on noticeboards at community hospitals. Summary statistics are shown in Table 1.

TABLE 1

| Evaluation of Baseline Characteristics Mean (SD) or Frequency (%) | | | | | |
|---|---|---|---|---|---|
| Study Group | | Sequence 1 (n = 22) | Sequence 2 (n = 23) | Overall | ANOVA (p-value) |
| Gender | Male | 10 (45.5%) | 11 (47.8%) | 21 (46.7%) | / |
|  | Female | 12 (54.5%) | 12 (52.2%) | 24 (53.3%) |  |
| Age (year) |  | 45.7 (12.3) | 47.5 (15.6) | 46.6 (14.0) | 0.664 |
| Weight (kg) |  | 72.4 (19.9) | 66.7 (14.3) | 69.5 (17.3) | 0.272 |
| Height (cm) |  | 167.5 (9.4) | 166.4 (8.0) | 166.9 (8.6) | 0.695 |
| BMI (kg/m$^2$) |  | 25.4 (4.6) | 24.0 3.7 | 24.6 4.2 | 0.226 |
| Body Temperature (° C.) |  | 36.9 (0.1) | 36.8 (0.2) | 36.8 (0.2) | 0.207 |
| Diastolic pressure (mmHg) |  | 76.1 (5.2) | 75.5 (6.5) | 75.8 (5.8) | 0.748 |
| Systolic pressure (mmHg) |  | 124.6 (6.7) | 121.2 (8.8) | 122.9 (7.9) | 0.145 |

Interventions

A2 beta-casein only milk and conventional milk were provided by A2 Infant Nutrition Limited (Auckland, New Zealand), and were distributed to the study site by SPRIM China. Staff at SPRIM China repackaged and labelled all of the products to ensure the investigators and subjects were blinded to which product they received in each intervention period. In each intervention period, the subjects were instructed to consume 250 ml of milk after 2 meals per day for 14 days. Subjects used a diary to record milk intake and adherence to each intervention. Used and unused cartons were collected at each visit to evaluate compliance with the interventions and to confirm that the blinding was intact. Subjects were randomised, with stratification by gender, to sequence 1 (conventional milk→A2 beta-casein only milk) or sequence 2 (A2 beta-casein only milk→conventional milk) according to the allocation number filed in sealed envelopes. The allocation was based on a computer-generated list prepared by SPRIM China.

A2 beta-casein only milk contained (per 100 ml) 271 kJ energy, 3.1 g protein, 3.6 g fat, 5.0 g carbohydrate, 48 mg sodium, 150 mg potassium, and 117 mg calcium. The ratio of A1 beta-casein to A2 beta-casein was approximately 40:60 in the A1/A2 product, as confirmed by ultra-performance liquid chromatography and mass spectrometry. Both products were identical and contained the same amount of protein.

The consumption of dairy products other than those provided was prohibited during the study. Subjects were permitted to consume non-dairy milk products, but not cows' milk during each washout period.

Subjects

The inclusion criteria were as follows: male or female; age 25-68 years; irregular milk consumption (as documented using a food frequency questionnaire); self-reported intolerance to commercial milk; self-reported mild to moderate digestive discomfort after milk consumption; and normal electrocardiograms (ECG) and blood pressure during quiet respiration. Subjects were enrolled if they: agreed not to take any medication, nutritional supplements, or other dairy products, including acidophilus milk, during the study; were willing to comply with all of the requirements and procedures; provided signed informed consent; agreed not to Subtle Cognitive Impairment Test (SCIT)

The SCIT is a computer-based test that measures the speed and effectiveness of information processing. Subjects indicated which of the two parallel vertical lines in the target stimulus is shorter, by pressing the left or right mouse button. The visually masked target stimulus was randomly presented at exposure durations of 16, 32, 48, 64, 80, 96, 112 and 128 ms; 12 trials at each for a total of 96 trials. Subject response time and error rate were recorded for stimulus exposure duration. Data for the four shortest exposure durations (16-64 ms) were pooled to provide two scores from the head of their respective response curves (pre-conscious-automatic processing): response time (SCIT-$RT_H$) and error rate (SCIT-$E_H$). Data for the four longer presentation durations (83-133 ms) were pooled to provide two scores for the tail of their respective response curves (conscious processing): response time (SCIT-$RT_T$) and error rate (SCIT-ET). The SCIT has high test-retest and internal consistency reliabilities and medium-high content validity.[20]

Statistical Analysis

The Kolmogorov-Smirnov Test was used to assess the normality of continuous variables. Non-normally distributed variables were subjected to square-root or log transformation to approximate a normal distribution. Baseline characteristics are presented descriptively as means±standard deviation (SD) or the number (percent) of subjects. SCIT variables were analysed using mixed-effects analysis of variance in which the allocated intervention and intervention period were included as fixed effects, and subject was included as a random effect nested within the study sequence (i.e., sequence 1, conventional milk→A2 beta-casein only milk; sequence 2, A2 beta-casein only milk→conventional milk). To investigate whether there were differences between the two interventions in the mean values for each endpoint, and whether the mean values changed during the study periods, Type III tests of fixed effects were used to tests the effects of the interventions and study periods. Additionally, contrast tests were performed to compare the mean values for each product. The presence of a carry-over effect was evaluated using the interaction Intervention× Period. If this interaction was not significant, data from both periods were evaluated. If the interaction was significant, only data from intervention period 1 were used.

TABLE 2

Mean (SD) for SCIT Response Time at Each Exposure Duration by Study Phase and Product

| Phase | Milk | Exposure Duration (ms) | | | | | | | | Head Mean | Tail Mean |
|---|---|---|---|---|---|---|---|---|---|---|---|
| | | 16 | 32 | 48 | 64 | 80 | 96 | 112 | 128 | | |
| Phase 1 | | | | | | | | | | | |
| Baseline | conventional | 517.5 | 463.6 | 449.3 | 432.7 | 424.3 | 427.0 | 422.7 | 421.9 | 459.5 | 424.0 |
| | | (145.6) | (87.3) | (50.1) | (46.8) | (41.1) | (37.1) | (34.3) | (32.1) | (63.4) | (32.2) |
| | A2 beta-casein only | 490.4 | 485.3 | 456.0 | 455.4 | 437.1 | 444.6 | 432.1 | 435.6 | 471.2 | 437.4 |
| | | (96.7) | (84.5) | (58.0) | (65.1) | (50.9) | (50.7) | (46.5) | (54.8) | (70.9) | (49.4) |
| Post-intervention | conventional | 459.7 | 465.2 | 441.6 | 447.7 | 447.1 | 447.3 | 441.2 | 444.7 | 452.8 | 445.1 |
| | | (53.1) | (52.4) | (37.7) | (43.5) | (36.5) | (39.6) | (36.0) | (31.3) | (41.5) | (31.2) |
| | A2 beta-casein only | 453.9 | 455.4 | 438.1 | 440.2 | 432.9 | 430.9 | 429.0 | 426.9 | 446.7 | 430.0 |
| | | (86.9) | (79.7) | (57.5) | (54.9) | (50.4) | (55.7) | (43.8) | (48.6) | (65.1) | (47.8) |
| Phase 2 | | | | | | | | | | | |
| Baseline | conventional | 443.0 | 439.7 | 441.1 | 436.6 | 426.4 | 427.4 | 431.1 | 428.9 | 440.3 | 428.5 |
| | | (66.5) | (56.8) | (68.9) | (55.1) | (44.8) | (50.0) | (50.6) | (53.5) | (60.0) | (47.4) |
| | A2 beta-casein only | 461.1 | 459.0 | 444.7 | 442.4 | 440.7 | 447.9 | 443.6 | 436.6 | 451.9 | 442.3 |
| | | (50.3) | (47.7) | (46.9) | (48.8) | (55.0) | (41.4) | (47.9) | (36.1) | (44.4) | (42.6) |
| Post-intervention | conventional | 449.8 | 459.7 | 436.5 | 431.6 | 432.4 | 427.6 | 417.2 | 428.4 | 443.5 | 426.3 |
| | | (64.6) | (77.1) | (53.4) | (47.3) | (52.6) | (42.3) | (42.7) | (42.9) | (55.7) | (42.9) |
| | A2 beta-casein only | 443.1 | 448.1 | 433.0 | 431.2 | 428.2 | 428.7 | 431.8 | 426.9 | 438.7 | 428.8 |
| | | (48.9) | (39.4) | (39.9) | (44.7) | (43.2) | (40.0) | (44.8) | (34.6) | (39.0) | (38.8) |

TABLE 3

Results of Mixed Effect ANOVA for SCIT Type III Test of Fixed Effects

| Outcomes | Effect | Num DF | Den DF | F Value | Pr > F |
|---|---|---|---|---|---|
| Response time | Product | 1 | 658 | 10.4 | 0.0013 ** |
| | Phase | 1 | 14 | 3.89 | 0.0686 |
| | Sequence | 1 | 43 | 0.24 | 0.63 |
| | Baseline value | 1 | 658 | 41.87 | <.0001 *** |
| Head mean of response time | Product | 1 | 42 | 1.42 | 0.2405 |
| | Phase | 1 | 42 | 0.00 | 0.9634 |
| | Sequence | 1 | 43 | 0.00 | 0.9604 |
| | Baseline value | 1 | 42 | 39.47 | <.0001 |
| Tail mean of response time | Product | 1 | 42 | 5.25 | 0.027 * |
| | Phase | 1 | 42 | 3.92 | 0.0542 |
| | Sequence | 1 | 43 | 1.64 | 0.2066 |
| | Baseline value | 1 | 42 | 54.37 | <.0001 *** |
| Error rate | Product | 1 | 658 | 12.6 | 0.0004 *** |
| | Phase | 1 | 14 | 0.07 | 0.7944 |
| | Sequence | 1 | 43 | 0.82 | 0.3699 |
| | Baseline value | 1 | 658 | 20.74 | <.0001 *** |
| Head mean of error rate | Product | 1 | 42 | 5.85 | 0.02 * |
| | Phase | 1 | 42 | 0.81 | 0.3741 |
| | Sequence | 1 | 43 | 2.03 | 0.1611 |
| | Baseline value | 1 | 42 | 8.04 | 0.007 ** |
| Tail mean of error rate | Product | 1 | 42 | 0.58 | 0.4514 |
| | Phase | 1 | 42 | 0.02 | 0.8984 |
| | Sequence | 1 | 43 | 0.62 | 0.434 |
| | Baseline value | 1 | 42 | 5.35 | 0.0257 * |

\* $p < 0.05$;
\*\* $p < 0.01$;
\*\*\* $p < 0.001$;
no symbol: $p \geq 0.05$

TABLE 4

Results of Mixed Effect ANOVA for SCIT Difference of Least Square Means

| | Difference of Least Squares Means (conventional minus A2 beta-casein only) | | | | |
|---|---|---|---|---|---|
| Outcome | Estimates | SD | DF | t Value | Pr > \|t\| |
| Response time | 8.5798 | 2.6605 | 658 | 3.22 | 0.0013 ** |
| Head mean of response time | 10.8330 | 9.0995 | 42 | 1.19 | 0.2405 |
| Tail mean of response time | 14.7353 | 6.4309 | 42 | 2.29 | 0.0270 * |
| Error rate | 1.759% | 0.496% | 658 | 3.55 | 0.0004 *** |
| Head mean of error rate | 2.758% | 1.140% | 42 | 2.42 | 0.0200 * |
| Tail mean of error rate | 0.402% | 0.529% | 42 | 0.76 | 0.4514 |

\* $p < 0.05$;
\*\* $p < 0.01$;
\*\*\* $p < 0.001$;
no symbol: $p \geq 0.05$

Example 2: Milk Trial and SCIT Analysis in Preschool Children

This trial was conducted according to the same methodology as for Example 1 above except that the subjects were preschool-aged children. The trial began with 80 subjects, but reduced to 75 as 5 children withdrew during the trial.

All analyses were carried out using a linear mixed model analysis for crossover design. In the main analyses there are three factors:

1. Phase (phase 1 and phase 2 of the crossover design)
2. Milk Type (mixed and A2 beta-casein only)
3. Condition (baseline and treatment), i.e. performance pre- and post-the consumption of milk.

Four SCIT measures were used as head and tail response times and head and tail error rates. Head and tail respectively refer to responses to stimuli presented at exposure durations between 16-64 ms (Head) and between 80-128 ms (Tail). This division corresponds to exposure durations at which only automatic processes are available for stimulus processing (Head) and exposure durations at which controlled (attention driven) processes are also available (Tail). Analyses were carried out separately for each of the four SCIT measures. The results are shown in FIGS. 3-5.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

REFERENCES

1. WO 1996/014577
2. WO 1996/036239
3. WO 2002/019832
4. WO 2014/193248
5. WO 2015/005804
6. WO 2015/026245
7. WO 2002/019832
8. Cade R, Privette M, Fregly M, Rowland N, Sun Z, Zele V, et al. Autism and schizophrenia: intestinal disorders. Nutr Neurosci. 2000; 3: 57-72.
9. Reichelt K L, Ekrem J, Scott H. Gluten, milk proteins and autism: dietary intervention effects on behavior and peptide secretion. J Appl Nutr. 1990; 42: 1-11.
10. Reichelt K L, Knivsberg A M. Can the pathophysiology of autism be explained by the nature of the discovered urine peptides? Nutr Neurosci. 2003; 6(1): 19-28.
11. Kawashti M I, Amin O R, Rowehy N G. Possible immunological disorders in autism: concomitant autoimmunity and immune tolerance. Egypt J Immunol. 2006; 13(1): 99-104.
12. Sokolov O, Kost N, Andreeva O, Korneeva E, Meshavkin V, Tarakanova Y, et al. Autistic children display elevated urine levels of bovine casomorphin-7 immunoreactivity. Peptides. 2014; 56: 68-71.
13. Tveiten D, Finvold A, Andersson M, Reichelt K L. Peptides and exorphins in the autism spectrum. Open J Psychiatry. 2014; 3(3): 275-87.
14. Dohan F C. Genetic hypothesis of idiopathic schizophrenia: its exorphin connection. Schizophr Bull. 1988; 14(4): 489-94.
15. Niebuhr D W, Li Y, Cowan D N, Weber N S, Fisher J A, Ford G M, et al. Association between bovine casein antibody and new onset schizophrenia among U S military personnel. Schizophr Res. 2011; 128(1-3): 51-5.
16. Reichelt K L, Landmark J. Specific IgA antibody increases in schizophrenia. Biol Psychiatry. 1995; 37(6): 410-3.
17. Severance E G, Dickerson F B, Halling M, Krivogorsky B, Haile L, Yang S, et al. Subunit and whole molecule specificity of the anti-bovine casein immune response in recent onset psychosis and schizophrenia. Schizophr Res. 2010; 118(1-3): 240-7.
18. Severance E G, Lin J, Sampson H A, Gimenez G, Dickerson F B, Halling M, et al. Dietary antigens, epitope recognition, and immune complex formation in recent onset psychosis and long-term schizophrenia. Schizophr Res. 2011; 126(1-3): 43-50.
19. Sun Z, Cade R J. A peptide found in schizophrenia and autism causes behavioral changes in rats. Autism. 1999; 3(1): 85-95.
20. Sun Z, Cade R J, Fregly M J, Privette R M. b-casomorphin induces Fos-like immunoreactivity in discrete brain regions relevant to schizophrenia and autism. Autism. 1999; 3(67-83).
21. Kost N V, Sokolov O Y, Kurasova O B, Dmitriev A D, Tarakanova J N, Gabaeva M V, et al. Beta-casomorphins-7 in infants on different type of feeding and different levels of psychomotor development. Peptides. 2009; 30(10): 1854-60.
22. Bruce, K M, Robinson, S R, Smith, J A and Yelland, G W Validity of a screening tool for detecting subtle cognitive impairment in the middle-aged and elderly. Clinical Interventions in Aging. 2014, 9, 2165-2176.

The invention claimed is:

1. A method of improving the cognitive function of a human free of diagnosed neurological conditions and having a diet comprising conventional milk, the method comprising administering to the human an amount of a composition containing beta-casein, wherein at least 90% by weight of the beta-casein is a beta-casein variant that does not produce beta-casomorphin-7 (BCM-7) on digestion in the gut of the human, such that cognitive function is improved.

2. The method as claimed in claim 1, wherein the beta-casein variant is A2 beta-casein, A3 beta-casein, D beta-casein, E beta-casein, H2 beta-casein or I beta-casein.

3. The method as claimed in claim 1, wherein the beta-casein variant is A2 beta-casein.

4. The method as claimed in claim 1, wherein the beta-casein comprises at least 90% by weight A2 beta-casein.

5. The method as claimed in claim 1, wherein the beta-casein comprises 100% A2 beta-casein.

6. The method as claimed in claim 1, wherein cognitive function is assessed using any one or more of Subtle Cognitive Impairment Test (SCIT), Automated Cognitive Test (ACT), Automated Neuropsychological Assessment Metrics (ANAM), Cognitive Drug Research Computerised Assessment System for Dementia (COGDRAS-D), Community Screening Instrument for Dementia (CSI-D), Computer-Administered Neuropsychological Screen for Mild Cognitive Impairment (CANS-MCI), Computer Assessment of Mild Cognitive Impairment (CAMCI), Computerised Self-Test (CST), Florida Brief Memory Scale (FBMS), Mild Cognitive Impairment (MCI), Neuropsychological Test Battery (NTB), Brief Assessment of Cognition in Schizophrenia (BACS), Cambridge Mental Disorders of the Elderly Examination-Revised (CAMDEX-R), Cambridge Neuropsychological Test Automated Battery (CANTAB), Computerised Multiphasic Interactive Neurocognitive Dual Display System (CMINDS), Computerised Neuropsychological Test Battery (CNTB), Memory Capacity Test (MCT), Neuropsychological Assessment Battery (NAB), Alzheimer's Disease Cooperative Study (ADCS), Executive, Linguistic, Spatial and Memory Abilities Battery (ELSMEM), Mini Mental State Examination (MMSE), and Hamilton D cognitive test (HAM-D).

7. The method as claimed in claim 1, wherein the composition is milk or a milk product.

8. The method as claimed in claim 7, wherein the milk is fresh milk, milk powder, liquid milk reconstituted from powder, skim milk, homogenised milk, condensed milk, evaporated milk, pasteurised milk, or non-pasteurised milk.

9. The method as claimed in claim 7, wherein the milk product is cream, yoghurt, quark, cheese, butter, or ice cream.

10. A method of preventing or treating cognitive impairment in a human in need thereof and free of diagnosed neurological conditions and having a diet comprising conventional milk, the method comprising administering to the human an amount of a composition containing beta-casein, wherein at least 90% by weight of the beta-casein is a beta-casein variant that does not produce beta-casomorphin-7 (BCM-7) on digestion in the gut of the human.

* * * * *